United States Patent [19]

Peterson

[11] 4,193,132
[45] Mar. 18, 1980

[54] RAIN-SHIELDED WELDER'S MASK

[76] Inventor: Edwin E. Peterson, 4109 Chenowith, The Dalles, Oreg. 97058

[21] Appl. No.: 945,552

[22] Filed: Sep. 25, 1978

[51] Int. Cl.$^2$ .............................................. A61F 9/06
[52] U.S. Cl. ............................................................ 2/8
[58] Field of Search .............. 2/8, 9, 10, 424, DIG. 5, 2/434, 438

[56] References Cited

U.S. PATENT DOCUMENTS

| 2,352,417 | 6/1944 | Thorson | 2/8 |
| 3,308,477 | 3/1967 | Boyd | 2/8 |

FOREIGN PATENT DOCUMENTS 1154740  6/1969  United Kingdom .............................. 2/8

Primary Examiner—Peter P. Nerbun
Attorney, Agent, or Firm—Eugene D. Farley

[57] ABSTRACT

A rain-shielded welder's mask assembly comprises in combination a head piece, a welder's mask with eye piece, and pivotal mounting means attaching the mask to the head piece.

A rain shield is mounted pivotally above the eye piece and connected to the head piece for raising and lowering upon relative angular movement of the mask with respect to the head piece. In its raised position it extends horizontally above the eye piece protecting the same from rain in the operative position of the mask. In its lowered position it nests over the eye piece, protecting it from rain in the raised inoperative position of the mask. A gutter is mounted on the front of the mask above the eye piece for diverting rain water therefrom. The welder thus is enabled to work steadily in rain conditions without stopping frequently to clean the eye piece of his mask.

6 Claims, 4 Drawing Figures

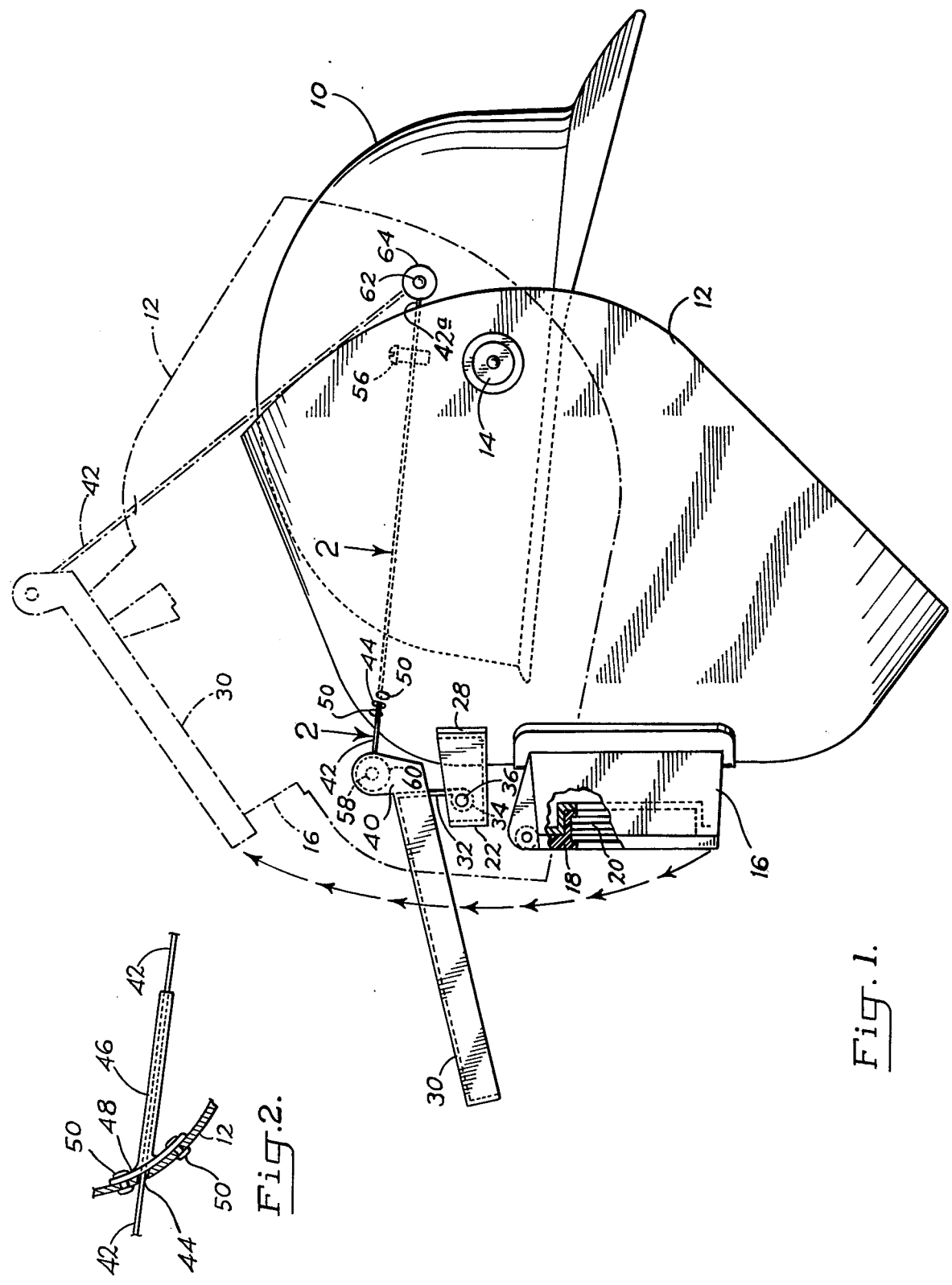
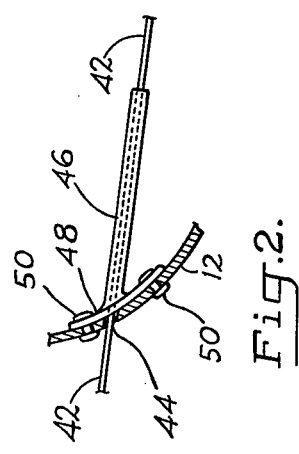

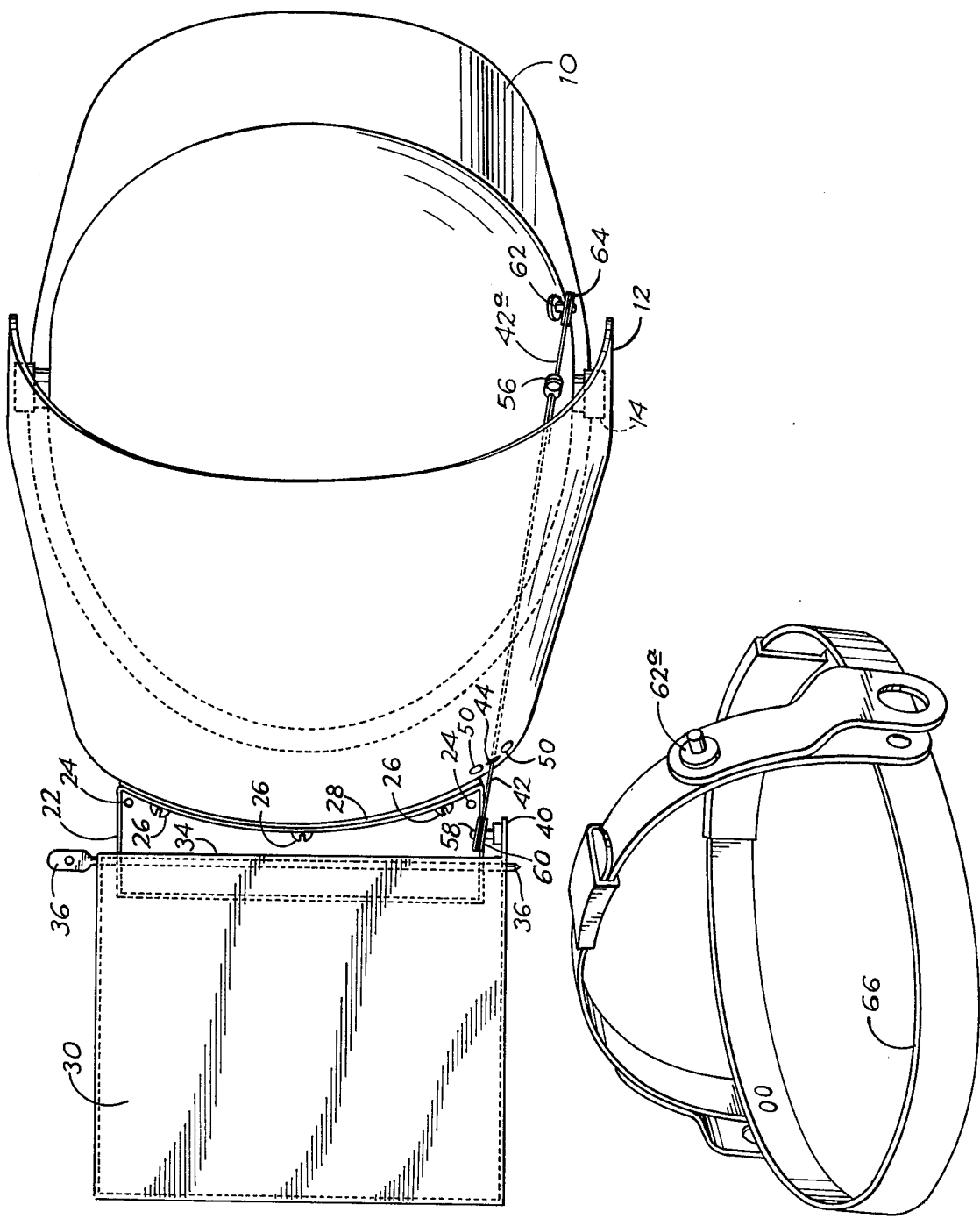

RAIN-SHIELDED WELDER'S MASK

BACKGROUND AND GENERAL STATEMENT OF THE INVENTION

This invention relates to welder's masks. It pertains particularly to welder's masks having eye pieces which are shielded from rain.

In the welding trade a problem is presented in that it is difficult for the welder to work under rainy conditions because of rain falling on the eye piece of his mask and impairing his vision. It accordingly is necessary for him to stop work at frequent intervals and clean the eye piece.

This is difficult because the conventional eye piece contains at least three lenses contained in a housing which permits access of rain water to the areas between the lenses. Accordingly, it is necessary for the welder to disassemble the eye piece, wipe each lens dry, and reassemble the eye piece before he can proceed.

This is so time consuming that it is conventional for welders to cease work in rainy weather, or to work under shelters especially provided.

Prior art patents addressed to a solution of this problem include the following:

| | | |
|---|---|---|
| Krogel | U.S. Pat. No. 2,394,388 | SHIELD FOR WELDER'S HELMETS |
| Boyd | U.S. Pat. No. 3,308,477 | SHIELD FOR WELDER'S HELMETS |
| Tate | U.S. Pat. No. 3,308,478 | HEAD PIECE |
| Wenzel | U.S. Pat. No. 3,368,220 | WELDER'S MASK |

The foregoing and other prior art references have not been successful, however, in overcoming the various problems attending the use of a welder's mask in rainy weather and it accordingly is the primary object of the present invention to provide such a mask which effectively shields the mask eye piece from rain in both raised and lowered positions of the mask and in various positions of the welder's head.

Another object of the present invention is to provide a rain shield for a welder's mask which may be taken off easily when not needed and put back on when needed.

Another object of the present invention is the provision of a rain shield for a welder's mask which may be applied to the various conventional head pieces used by welders, including hard hats and simple head bands, or hard hat liners.

Another object of the present invention is the provision of a welding helmet rain shield which, as opposed to one actuated by means of a counter weight, is positively driven between its raised and lowered positions.

Another object of the present invention is the provision of a welding helmet rain shield driven between its raised and lowered positions by the relative angular movement of the mask and head piece.

Another object of the present invention is the provision of a welding helmet rain shield which effectively shields the mask eye piece in both the raised and lowered positions of the shield.

Still another object of this invention is the provision of a welder's mask having a rain shield which in its operative position permits removal of the eye piece as required when the welder wishes to chip off the slag from his weld with the welding hood down and the welding shield up.

The foregoing and other objects of this invention are accomplished by means of a welder's mask assembly which, generally stated, comprises a head piece, a welder's mask with an eye piece, and first pivotal mounting means attaching the mask to the head piece for relative angular movement between raised operative and lowered inoperative mask positions.

The assembly includes also a rain shield and second pivotal mounting means mounting the rain shield on the mask above the eye piece for angular movement between a rain shield raised position in which it extends substantially horizontally above the eye piece when the mask is lowered, and a rain shield lowered position in which it overlies the eye piece when the mask is raised. Substantially rigid link means interconnects the head piece and the rain shield and is operative to shift the rain shield between its raised and lowered positions upon relative angular movement of the mask and head piece.

DESCRIPTION OF PREFERRED EMBODIMENTS OF THE INVENTION

In the drawings:

FIG. 1 is a view in side elevation of the hereindescribed rain-shielded welder's mask assembly illustrating in full outline the mask lowered in operative position and in dashed outline the mask raised in inoperative position;

FIG. 2 is a detail sectional view taken along line 2—2 of FIG. 1;

FIG. 3 is a plan view of the rain-shielded welder's mask of FIG. 1; and

FIG. 4 is a top perspective view of an alternate type of head piece which may be used together with the rain shielded welder's mask of my invention, illustrating particularly the attaching means employed for attaching the mask to the head piece.

Referring first to the embodiments of FIGS. 1, 2 and 3:

In this embodiment the rain shielded welder's mask assembly of my invention is illustrated in its use with a conventional hard hat 10 such as is widely used by welders working under hazardous conditions.

A welder's mask 12 is pivotally attached to the head piece by means of conventional threaded fasteners 14.

As is usual, the mask comprises a molded piece having a top, a front face, and two side faces. On the front face it mounts a conventional eye piece 16 which mounts a hinged plate 18. The latter in turn mounts the three piece lens which is so difficult to clean as discussed hereinabove.

Plate 18, and accordingly lens 20, may be swung from its illustrated position outwardly to an open position. This adjustment is made by the welder when performing non-hazardous chores such as chipping the slag from his work, where he is not exposed to the intense light of his torch.

It is to be noted that shield 12 may be moved angularly with respect to head piece 10. This adjustment is made frequently by the welder as he works, as illustrated by the full line and dashed line positions of FIG. 1. The present invention makes use of this movement to drive a rain shield for the lens so that as the mask is moved from its lowered to its raised position the rain shield moves correspondingly and protects the lens from water in both mask positions.

The eye shield assembly includes a gutter 22, FIGS. 1 and 3, which overlies the eye piece. The gutter is trough-shaped and provided with drain holes 24. It is secured to the brow portion of the welder's mask by means of bolts or screws 26. A gasket 28 is interposed between the back rim of the gutter and the mask to seal off the area effectively, thereby preventing water from running down the face of the mask and onto the eye piece.

Gutter 22 is used as a support for hinge means which detachably mount a rain shield indicated at 30.

The rain shield is rectangular and downwardly dished so that it nests or cups over the outwardly projecting eye piece in its lowered position.

The flat top of rain shield 30 is formed with an extension 32 which extends downwardly into gutter 22. It in turn is shaped into the knuckle of a pin hinge indicated in FIG. 1 at 34.

A pin 36 extends through the side walls of gutter 22 and through knuckle 34, thereby forming a pin hinge assembly which pivotally mounts the rain shield in proper relation to the gutter 22 and eye piece 16.

The drive means for the rain shield comprises a rigid link means including as one member an upwardly extending lever 40 which is rigid to rain shield 30. A stiff link 42 extends through an opening 44 in the mask and runs rearwardly to the rear portion of the head piece 10. This link member may comprise a piece of stiff wire.

As shown in FIG. 2, a sleeve 46 on a stiffening plate 48 is secured by rivets 50 to the inner surface of the mask 12. The sleeve receives the link 42 in sliding, piston-like motion.

Preferably link 42 is segmented and includes a segment 42a with screw clamp 56. This enables longitudinal adjustment of the link as required to accommodate different helmet and head piece arrangements.

Pivotal mounting means interconnect the respective ends of link 42, 42a, with lever 40 and head piece 10. Grommet-type connecting means are preferred for this purpose since they provide a quick and easy means of connecting and disconnecting the link.

Accordingly, lever 40 mounts an inwardly projecting grommet post 58. The outer end of link 42 mounts a grommet 60 which is releasably applicable to the post.

In a similar manner hard hat 10 mounts a grommet post 62 while the inner end of link segment 42 mounts a grommet 64 which may be releasably applied to the grommet post.

FIG. 4 illustrates an alternate embodiment of the invention in which a conventional head band or hard hat liner 66 is used as a head piece. This may be desirable in non-hazardous conditions, for the comfort of the welder. The only modification required to adapt the liner to the purposes of the present invention is the addition of grommet post 62a. The only modification of helmet 10 for the purposes of the present invention is the provision of grommet post 62.

OPERATION

The operation of the hereindescribed rain-shielded welder's mask assembly is as follows:

To install a rain shield, gutter 22 is applied to the brow portion of the mask above eye piece 16. Link 42, 42a is threaded through opening 44 in the mask. One of its ends is snapped over grommet post 58 on lever 40. The other of its ends is snapped over grommet post 62 on hard hat 10.

The assembly then is ready for use. When the mask is lowered, shield 30 lies in a generally horizontal position above eye piece 16, protecting lens 20 from rain; FIG. 1, full line position. Gutter 22 collects water running down the mask and serves a similar function.

If the welder desires to open lens 20, he may do so and still have the lens protected from rain.

When the welder raises the mask, the resulting relative angular movement of mask and head piece generates a piston-like action in link member 42, 42a. Acting through lever 40, this pushes the rain shield 30 downwardly so that it assumes the dashed line position of FIG. 1 in which it nests over eye piece 16. The eye piece and lens 20 which it contains are protected from rain in both positions of the mask and the welder is able to continue his work in the rain without the necessity of frequently disassembling the eye piece and lens in order to wipe away accumulated rain water.

Having thus described my invention in preferred embodiments, I claim as new and desire to protect by Letters Patent:

1. A rain-shielded welder's mask assembly comprising in combination:
   (a) a head piece,
   (b) a welder's mask with outwardly projecting eye piece,
   (c) first pivotal mounting means releasably attaching the mask to the head piece for relative angular movement between raised inoperative and lowered operative mask positions,
   (d) a dished rain shield dimensioned to nest over the eye piece,
   (e) a gutter secured to the mask above the eye piece,
   (f) pin hinge means connecting the rain shield to the gutter for angular movement between a rain shield raised position in which it extends substantially horizontally above the eye piece when the mask is lowered and a rain shield lowered position in which it nests over the eye piece when the mask is raised,
   (g) a lever extending upwardly from the inner end of the rain shield,
   (h) a substantially rigid link, and
   (i) detachable grommet-type connecting means connecting the respective ends of the link one to the lever and the other to the head piece,
   (j) the link extending rearwardly from the rain shield through an opening in the mask and thence rearwardly between the mask and head piece to its rearward connection to the head piece.

2. A rain-shielded welder's mask assembly comprising, in combination:
   (a) a head piece having lateral sides,
   (b) a welder's mask spaced outwardly from the head piece and having lateral sides and a front provided with an eye piece,
   (c) first pivotal mounting means attaching the sides of the mask to the sides of the head piece for relative angular movement between raised inoperative and lowered operative mask positions,
   (d) a rain shield,
   (e) second pivotal mounting means mounting the rain shield on the mask above the eye piece for angular movement between a rain shield raised position in which it extends substantially horizontally above the eye piece when the mask is lowered and a rain shield lowered position in which it overlies the eye piece when the mask is raised, and
   (f) substantially rigid elongated link means connected at its forward end to the rain shield on a pivot axis spaced from the axis of the second pivotal mounting means, and at its rearward end to the head piece at a point spaced from the axis of the first pivotal mounting means, (g) the elongated link means extending rearwardly from the rain shield through an opening in the mask and thence rearwardly between the mask and head piece to its rearward connection to the head piece.

3. The combination of claim 2 wherein the first pivotal mounting means and the connection of the link means to the head piece are detachable, allowing interchange of head pieces.

4. The combination of claim 2 including a rain gutter secured to the mask between the eye piece and the inner end of the rain shield, for preventing water from running down the mask onto the eye piece.

5. The combination of claim 4 wherein the second pivotal mounting means comprises a downward extension on the inner end of the rain shield connected pivotally to the gutter.

6. A rain-shielded welder's mask assembly comprising, in combination:

(a) a head piece,
(b) a welder's mask having a front provided with an eye piece,
(c) first pivotal mounting means releasably attaching the mask to the head piece for relative angular movement between raised inoperative and lowered operative mask positions;
(d) a rain shield,
(e) a rain gutter secured to the mask between the eye piece and the inner end of the rain shield, for preventing water from running down the mask onto the eye piece,
(f) an extension on the inner end of the rain shield connected pivotally to the gutter for angular movement of the rain shield between a rain shield raised position in which it extends substantially horizontally above the eye piece when the mask is lowered and a rain shield lowered position in which it overlies the eye piece when the mask is raised, and
(g) substantially rigid elongated link means connected at its forward end to the rain shield on a pivot axis spaced from the axis of the pivot connection to the gutter, and at its rearward end detachably to the head piece at a point spaced from the axis of the first pivotal mounting means.

* * * * *